US012636774B2

(12) United States Patent
Yoon

(10) Patent No.:  US 12,636,774 B2
(45) Date of Patent:      May 26, 2026

(54) ARM ASSEMBLY FOR SURGICAL ROBOT

(71) Applicant: MEERE COMPANY INC.,
Hwaseong-si (KR)

(72) Inventor: Du Ho Yoon, Seoul (KR)

(73) Assignee: MEERE COMPANY INC.,
Hwaseong-si (KR)

( * ) Notice: Subject to any disclaimer, the term of this
patent is extended or adjusted under 35
U.S.C. 154(b) by 310 days.

(21) Appl. No.: 18/202,500

(22) Filed: May 26, 2023

(65) Prior Publication Data

US 2023/0381952 A1      Nov. 30, 2023

(30) Foreign Application Priority Data

May 27, 2022    (KR) ........................ 10-2022-0065481

(51) Int. Cl.
*A61B 34/30*        (2016.01)
*A61B 34/37*        (2016.01)
*B25J 9/10*          (2006.01)
*B25J 13/06*        (2006.01)

(52) U.S. Cl.
CPC ............... *B25J 9/104* (2013.01); *A61B 34/37*
(2016.02); *B25J 13/06* (2013.01)

(58) Field of Classification Search
CPC ........... A61B 34/37; A61B 34/71; B25J 9/104
See application file for complete search history.

(56) References Cited

U.S. PATENT DOCUMENTS

| | | | | |
|---|---|---|---|---|
| 8,105,233 B2 * | 1/2012 | Abou El Kheir .. | A61B 1/00097 |
| | | | 600/173 |
| 10,595,948 B2 * | 3/2020 | Solomon ................ | A61B 34/37 |
| 2013/0239392 A1 * | 9/2013 | Solomon .................. | F16H 7/20 |
| | | | 29/428 |
| 2016/0345801 A1 * | 12/2016 | Kishi ...................... | A61B 34/30 |
| 2018/0079074 A1 * | 3/2018 | Devengenzo .......... | A61B 34/71 |

FOREIGN PATENT DOCUMENTS

JP          H11-280864 A      10/1999

* cited by examiner

*Primary Examiner* — Eric D. Bertram
(74) *Attorney, Agent, or Firm* — Dinsmore & Shohl LLP;
Yongsok Choi, Esq.

(57)                    ABSTRACT

Provided is an arm assembly for a surgical robot. The arm
assembly for the surgical robot having a plurality of robot
arms, includes a first pulley attached to one side of each
robot arm, a second pulley attached to the other side of the
robot arm to be spaced apart from the first pulley, and a first
strap of which one end is connected to the first pulley and the
other end is connected to the second pulley, wherein a
position of one end of the first strap is fixed to the first pulley
and a position of the other end of the first strap is adjustable
on the second pulley.

2 Claims, 11 Drawing Sheets

ARM ASSEMBLY FOR SURGICAL ROBOT

CROSS-REFERENCE TO RELATED APPLICATION

This application is based on and claims priority under 35 U.S.C. § 119 to Korean Patent Application No. 10-2022-0065481, filed on May 27, 2022, in the Korean Intellectual Property Office, the disclosure of which is incorporated by reference herein in its entirety.

BACKGROUND

1. Field

The present disclosure relates to an arm assembly for a surgical robot, which may be applied to a surgical robot system.

2. Description of the Related Art

A surgical robot refers to a robot capable of performing surgical action on behalf of a surgeon who has performed the surgical action. Such a surgical robot may perform accurate and precise operations as compared with human beings and may perform a remote surgery. Surgical robots that are currently being developed worldwide may include bone surgery robots, laparoscopic surgery robots, stereotactic surgery robots, etc.

The surgical robot is provided with at least one robot arm, and a robotic surgical instrument is attached to a front end of each robot arm. The robotic surgical instrument is inserted into the body of a patient through an incision point of the patient. On the other hand, the robot arm is located outside the incision point, and while the surgery is carried out, the robot arm maintains position and posture of the robotic surgical instrument.

In an internal structure of a general robot arm, a pulley-belt structure transferring a driving force to an end effector generally has a structure in which a tension adjustor protrudes out of a pulley, and thus, there may be abrasion and damage to a belt.

Also, the above structure is away from a miniaturization tendency of a surgical robot, and then, a volume of the robot arm may increase and the body of the surgical robot may expand.

SUMMARY

The present disclosure provides a robot arm assembly having a simple structure capable of configuring a manipulator and transferring a driving force to an instrument while a surgical robot performs a surgical operation.

Additional aspects will be set forth in part in the description which follows and, in part, will be apparent from the description, or may be learned by practice of the presented embodiments of the disclosure.

According to an aspect of the present disclosure, provided is an arm assembly for a surgical robot having a plurality of robot arms, includes a first pulley attached to one side of each robot arm, a second pulley attached to the other side of the robot arm to be spaced apart from the first pulley, and a first strap of which one end is connected to the first pulley and the other end is connected to the second pulley, wherein a position of one end of the first strap is fixed to the first pulley and a position of the other end of the first strap is adjustable on the second pulley.

The arm may include a first block fixed to the first pulley and connected to one end of the first strap, and a second block which is attached to the second pulley, is connected to the other end of the first strap, and of which a position is adjustable on the second pulley.

The arm assembly may further include a connection member that is supported by the first pulley and is partially inserted in the first block so as to adjust the position of the first block.

One end of the first strap may extend along a surface of the first block, and the other end of the first strap may extend along a surface of the second block.

The arm assembly may further include a first connection tab that is attached to one end of the first strap and is supported by a first stopper protrusion of the first block, and a second connection tab that is attached to the other end of the first strap and is supported by a second stopper protrusion of the second block.

The arm assembly may further include a second strap of which one end is connected to the second pulley and the other end is connected to the first pulley, wherein a position of one end of the second strap may be fixed to the second pulley and a position of the other end of the second strap may be adjustable on the first pulley.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
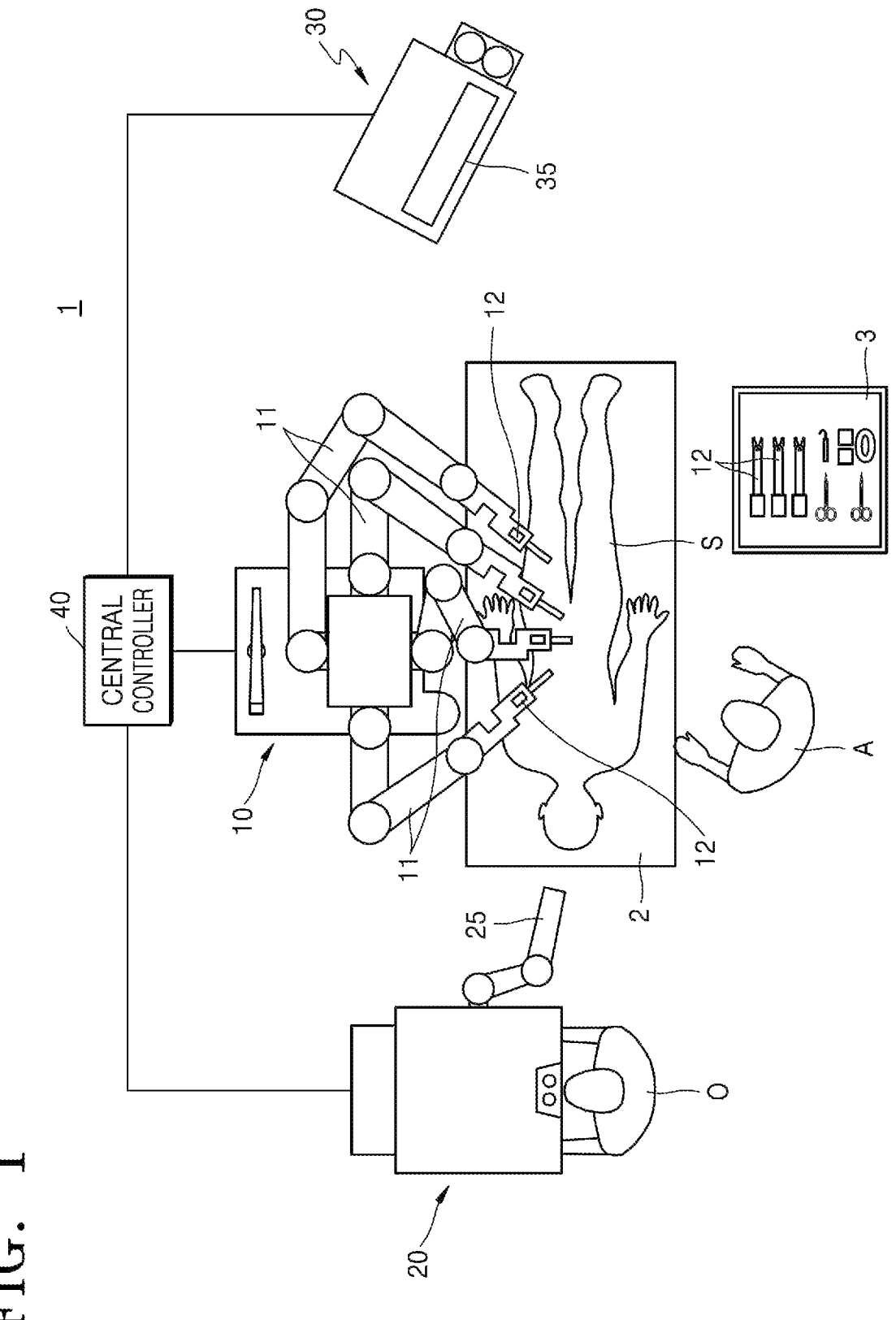
FIG. 1 is a plan view of an entire system of a surgical robot apparatus according to an embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

As the present disclosure allows for various changes and numerous embodiments, particular embodiments will be illustrated in the drawings and described in detail in the written description. However, this is not intended to limit the present disclosure to particular modes of practice, and it is to be appreciated that all modifications, equivalents, and/or alternatives that do not depart from the spirit and technical scope are encompassed in the disclosure. In describing the present disclosure, like reference numerals denote the same elements even when the elements are provided in another embodiment.

It will be understood that although the terms "first" and "second" are used herein to describe various elements, these elements should not be limited by these terms. Terms are only used to distinguish one element from other elements.

The terms used in the present specification are merely used to describe particular embodiments, and are not intended to limit the present disclosure. In the present specification, it is to be understood that the terms such as "including," "having," and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Hereinafter, one or more embodiments will be described in detail with reference to accompanying drawings.

Hereinafter, a robot arm assembly and structure may be applied to various robots that are industrially available. The robot arm assembly and structure may be applied to various types of robot devices and robot systems, e.g., industrial robots, medical robots, mobile robots, etc.

That is, the robot arm assembly and structure according to the present disclosure are not limited to a certain shape, space, or usage, and may be applied to various structures in which a plurality of links or arms are connected. However, an example in which the robot arm structure is installed in a surgical robot will be described below for convenience of description.

FIG. 1 is a plan view of an entire system of a surgical robot apparatus 1 according to an embodiment of the present disclosure.

Referring to FIG. 1, the surgical robot apparatus 1 may include a manipulator 10 performing surgery on a patient S lying on an operating table 2, and a master console 20 allowing an operator 0 to remotely control the manipulator 10. Also, the surgical robot apparatus 1 may include a vision cart 30. An assistant A may check the progress of the surgery through a display unit 35 of the vision cart 30.

The manipulator 10 may include at least one robot arm assembly 11 for surgical robot. In general, a robot arm has a similar function to that of an arm and/or a wrist of a human being, and denotes a device having a wrist to which a certain tool may be attached. In the specification herein, the robot arm assembly 11 for the surgical robot may be defined as a concept encompassing such elements as an upper arm, a lower arm, a wrist, and an elbow, and a surgical instrument coupled to the wrist, etc. The robot arm assembly 11 for the surgical robot of the manipulator 10 as above may be implemented to operate with multiple degrees of freedom. The robot arm assembly 11 for the surgical robot may include an instrument 12 inserted into a surgical site of the patient S, a yaw driving unit for rotating the instrument 12 in a yaw direction according to the operating position, a pitch driving unit for rotating the instrument in a pitch direction that is perpendicular to the rotational driving of the yaw driving unit, a transport driving unit for moving the instrument 12 in a lengthwise direction, a rotation driving unit for rotating the instrument, and an instrument driving unit installed on an end of the instrument 12 to incise or cut a surgical lesion. However, the composition of the robot arm assembly 11 for the surgical robot is not limited thereto, and it is to be appreciated that such an example does not limit the scope of claims of the present disclosure. Here, the actual control procedures by which the robot arm assembly 11 for the surgical robot is rotated, moved, etc., when the operator 0 manipulates a manipulation lever will not be described in detail.

One or more manipulators 10 may be used to operate the patient S, and the instrument 12 allowing the surgical site to be displayed as an image through the display unit 35 may be implemented as an independent manipulator 10. Also, as described above, the embodiments of the present disclosure may be universally used in surgeries in which various surgical endoscopes (e.g., thoracoscopy, arthroscopy, parenteral, etc.) other than laparoscopy are used.

A robot arm 100 may be applied to a part of the arm assembly 11 for the surgical robot of the manipulator 10.

The master console 20 and the manipulator 10 are not necessarily provided as separate devices that are physically separated from each other, and may be combined and implemented integrally with each other. Hereinafter, a case in which the master console 20 and the manipulator 10 are physically separated from each other will be described below for convenience of description.

The master console 20 includes a manipulation lever (not shown) and a display member (not shown). Also, the master console 20 may additionally include an external display apparatus 25 for displaying the status of the operator 0.

In detail, the master console 20 includes manipulation levers (not shown) that may be held and manipulated by both hands of the operator 0. The manipulation lever may include two or more handles, and a manipulation signal according to the handle manipulation of the operator 0 is transferred to the manipulator 10 through a wired or wireless communication network to control the arm assembly 11 for the surgical robot. That is, surgical operations such as moving of a location, rotation, cut operation, etc. of the arm assembly 11 for the surgical robot may be performed by the operator 0 manipulating the handles.

For example, the operator 0 may manipulate the arm assembly 11 for the surgical robot or the instrument 12 by using the manipulation lever of a handle type. The manipulation lever as above may have various mechanical configurations according to the manipulation method thereof and may be provided in various types, for example, a master handle for manipulating operations of the arm assembly 11 for the slave surgical robot or the instrument 12, and various input units such as a joystick, a keypad, a trackball, or a touchscreen added to the master console 20 for manipulating functions of entire system, for operating the arm assembly 11 for the surgical robot of the manipulator 10 and/or other surgical instruments. Here, the manipulation lever is not limited to the shape of the handle, and may not be restricted to a certain shape provided that the manipulation lever has a shape capable of controlling operations of the arm assembly 11 for the surgical robot through a network such as a wired or wireless communication network.

An image captured by the instrument 12 is displayed on the display member of the master console 20. Also, the display member may display a certain virtual manipulation plate independently or together with the image captured by the instrument 12.

The display member may be provided in various types by which the operator 0 may check the image. For example, the display apparatus may be provided to correspond to both eyes of the operator 0. In another example, the display member may include one or more monitors such that information that is necessary during the surgery may be displayed on each monitor. The number of the display members may be determined depending on the type or kind of the information that needs to be displayed. The master console 20 will be described in more detail below.

The vision cart 30 is installed apart from the manipulator 10 or the master console 20, and the progress of the surgery may be checked through the display unit 35 from outside. The image displayed by the display unit 35 may be the same as the image displayed on the master console 20 of the operator 0. The assistant A may assist the surgery performed by the operator 0 while checking the image on the display unit 35. For example, the assistant A may replace the instrument 12 from an instrument cart 3 according to the progress of the surgery.

A central controller 40 is connected to the manipulator 10, the master console 20, and the vision cart 30 to receive/transmit signals from/to each of the manipulator 10, the master console 20, and the vision cart 30. The central controller 40 may be provided in one of the manipulator 10, the master console 20, and the vision cart 30, or may be independently provided.

Figure 2:
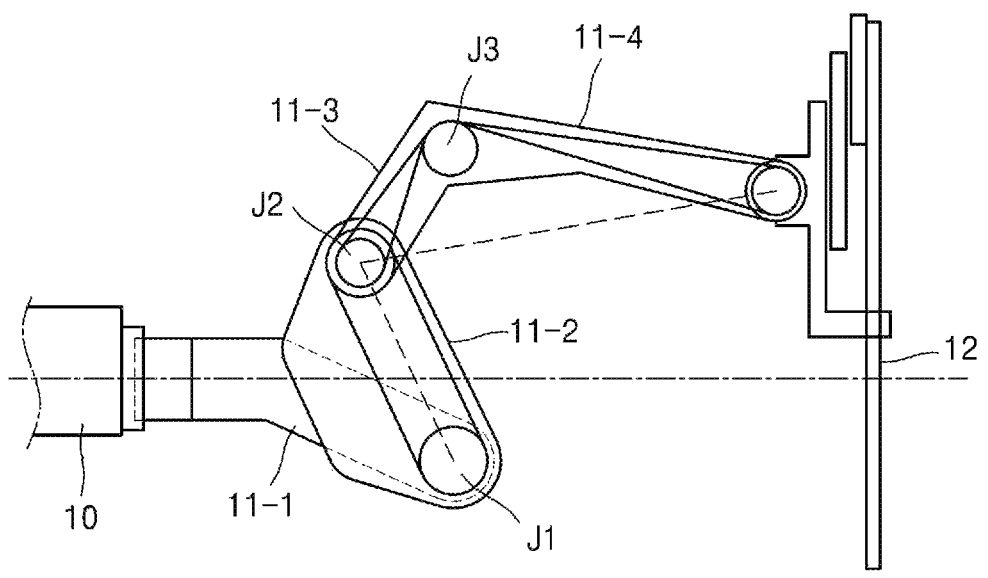
FIG. 2 is a perspective view of a manipulator in the surgical robot of FIG. 1.

FIG. 2 is a diagram of the manipulator 10 in the surgical robot of FIG. 1.

Referring to FIG. 2, the arm assembly 11 for the surgical robot may be formed by a plurality of robot arms connected to one another. The arm assembly 11 for the surgical robot may include a joint disposed between neighboring robot arms.

For example, the manipulator 10 may have a first arm 11-1, a second arm 11-2, a third arm 11-3, and a fourth arm 11-4.

The first arm 11-1 and the second arm 11-2 are connected via a first joint J1 and may be rotated about the first joint J1. Also, the second arm 11-1 and the third arm 11-3 are connected via a second joint J2 and may be rotated about the second joint J2.

For example, the third arm 11-1 and the fourth arm 11-4 may be formed as one body as shown in the drawing, and a third joint J3 may set a passage of a power transfer component therein. In another example, the third arm 11-3 and the fourth arm 11-4 may be separately provided and connected via the third joint J3.

The instrument 12 may be attached to an end portion of the fourth arm 11-4. An end effector (not shown) attached to the instrument 12 may generally include a device attached to an end portion of a robot to carry out required works, e.g., a gripper for gripping an object, a welder for performing a welding operation, a painter for performing a painting operation, and various surgical instrument for carrying out surgery.

Figure 3:
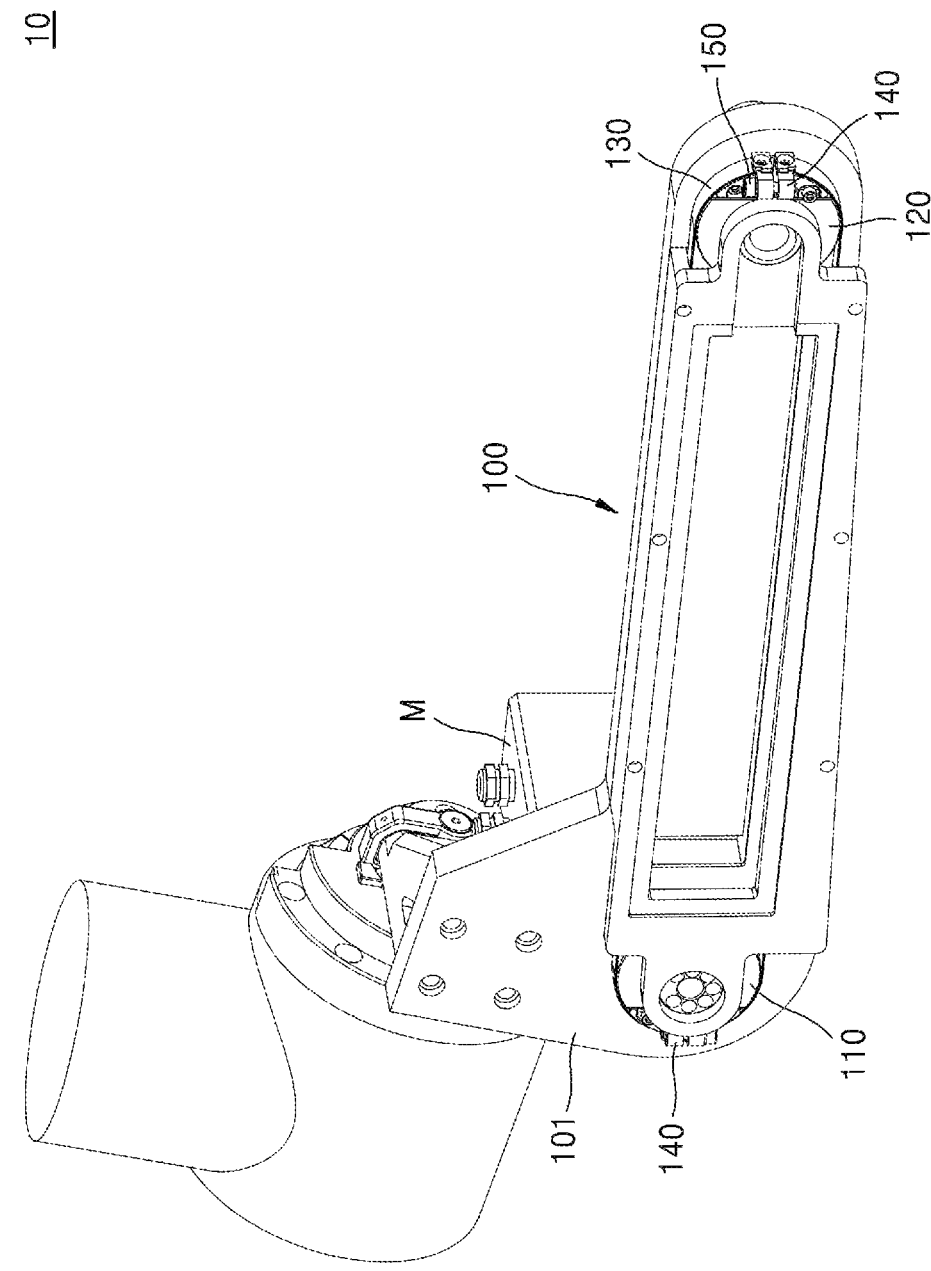
FIG. 3 is a perspective view of a surgical robot arm according to an embodiment of the present disclosure.

FIG. 3 is a perspective view of a surgical robot arm according to an embodiment of the present disclosure.

Referring to FIG. 3, the arm assembly 11 for the surgical robot may have a plurality of robot arms 100 connected thereto to form the manipulator 10. A plurality of robot arms

100 are connected so as to transfer the driving force via the joint disposed between the robot arms 100.

The arm assembly 11 for the surgical robot may include the plurality of robot arms 100. The joint forming a degree of freedom of rotation of the robot arm may be disposed between a pair of robot arms 100 connected to each other. The arm assembly 11 for the surgical robot may be connected to at least one actuator or a driving motor M in order to facilitate the control on the instrument 12.

In an embodiment, the arm assembly 11 for the surgical robot may include the plurality of robot arms 100, an arm body 101, and a driving motor M. The arm assembly 11 for the surgical robot is supplied with electric power from a driving unit such as the driving motor M and is rotated so as to perform surgery.

In an embodiment, the arm assembly 11 for the surgical robot may include the arm body 101 connected to one side of the robot arm 100. The arm body 101 is disposed between the robot arm 100 and the robot arm 100 to form a certain space, and the driving motor M that generates rotating power for rotating the robot arms 100 may be arranged in the space.

The driving motor M may be defined as various components transferring the driving force to the robot arm 100, for example, a reducer may be built therein or a separate reducer may be drivingly connected to the outside thereof.

Figure 4:
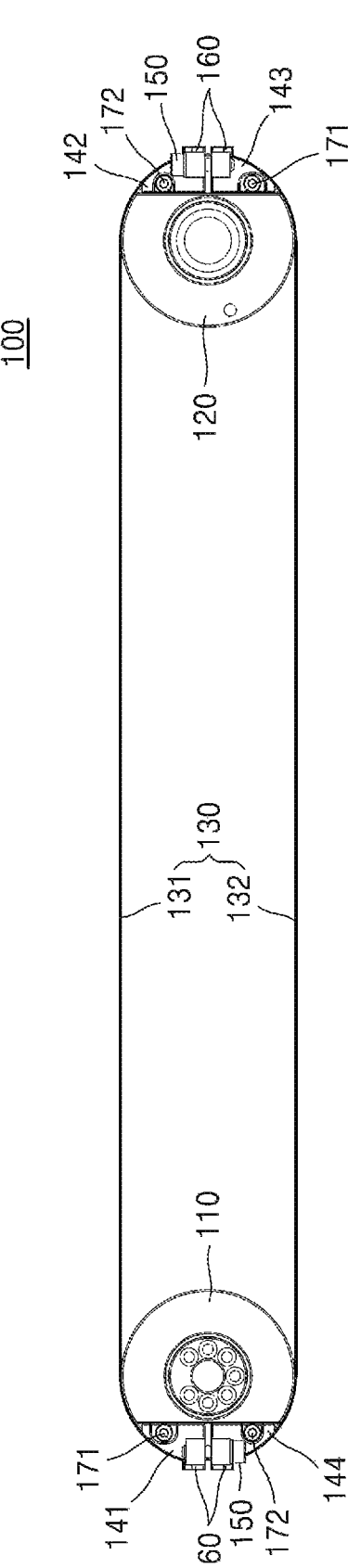
FIG. 4 is a diagram showing an arm assembly for a surgical robot according to an embodiment of the present disclosure.
Figure 5:
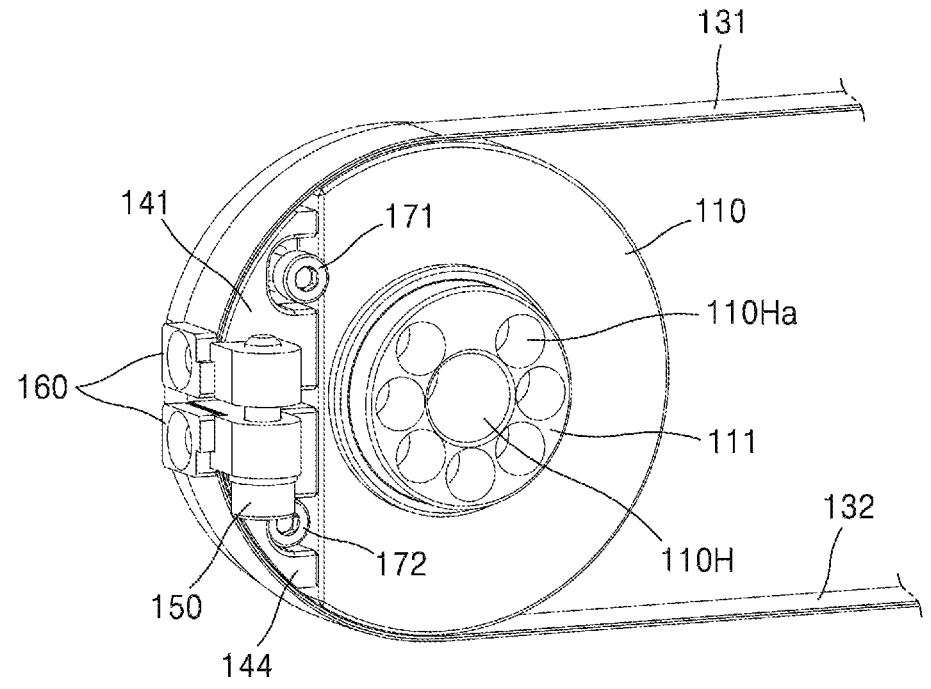
FIG. 5 is a perspective view showing one side of the arm assembly for the surgical robot of FIG. 4.
Figure 6:
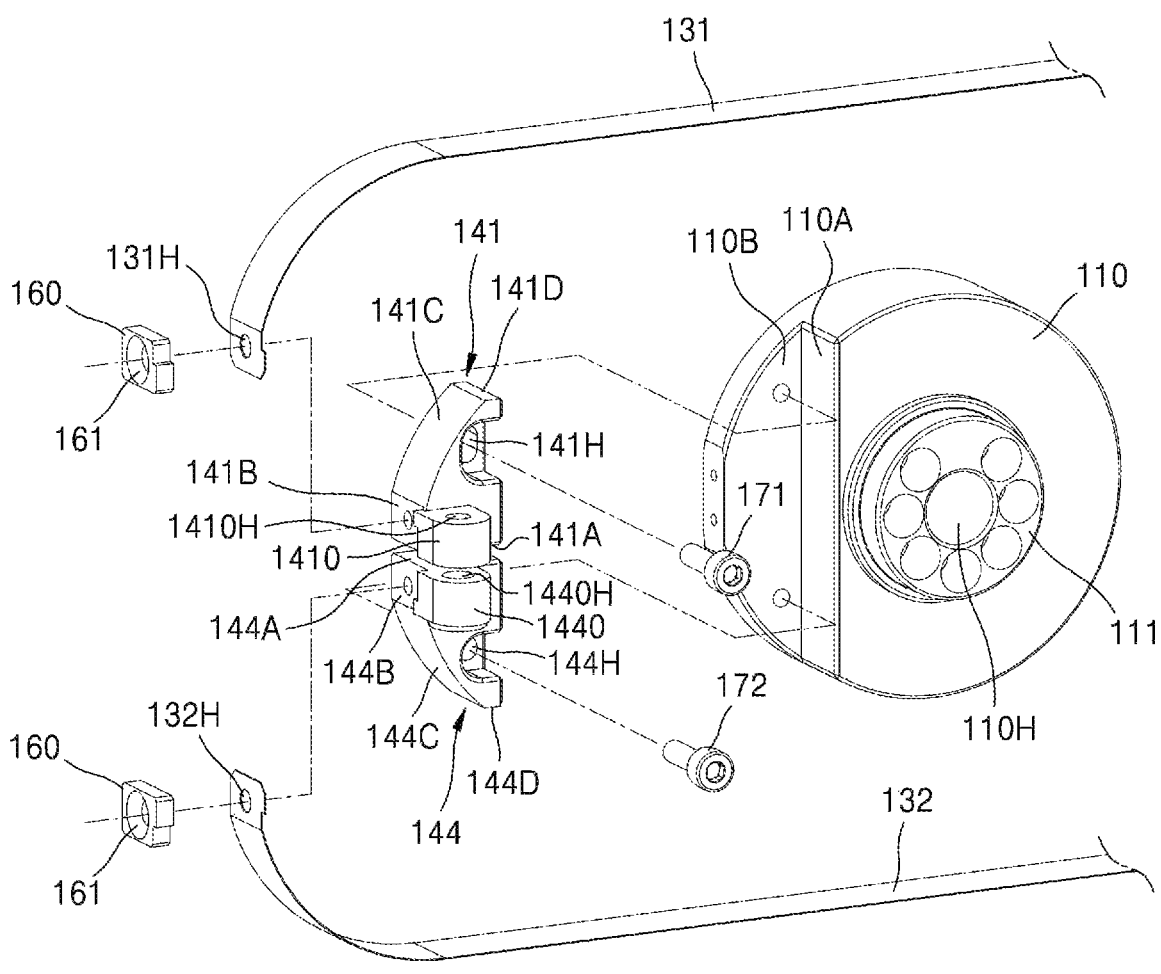
FIG. 6 is an exploded perspective view of the arm assembly for the surgical robot of FIG. 4.
Figure 7:
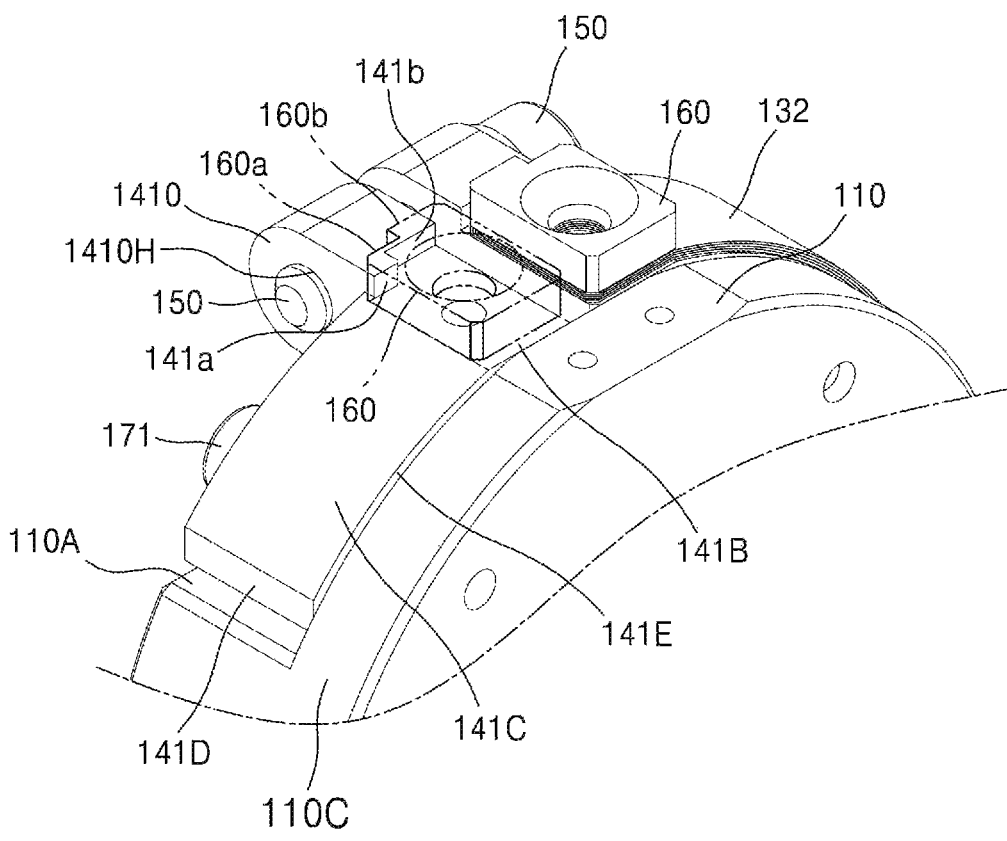
FIG. 7 is an enlarged view showing a part of FIG. 4.
Figure 8:
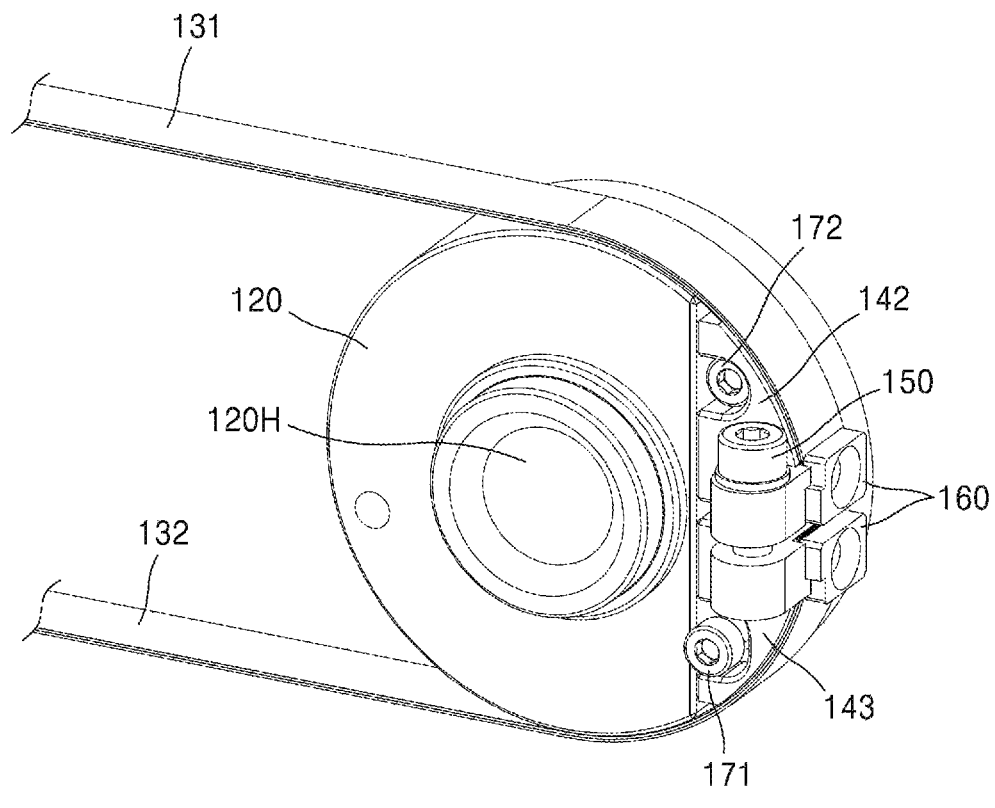
FIG. 8 is a perspective view showing the other side of the arm assembly for the surgical robot of FIG. 4.

FIG. 4 is a diagram of the arm assembly 11 for the surgical robot according to an embodiment of the present disclosure, FIG. 5 is a perspective view showing one side of the arm assembly for the surgical robot of FIG. 4, FIG. 6 is an exploded perspective view of the arm assembly for the surgical robot of FIG. 4, FIG. 7 is an enlarged view showing a part of FIG. 4, and FIG. 8 is a perspective view showing the other side of the arm assembly for the surgical robot of FIG. 4.

Referring to FIGS. 4 to 8, the arm assembly for the surgical robot may be provided with the plurality of robot arms 100, and each robot arm 100 may include a first pulley 110, a second pulley 120, a strap unit 130, block units 140, connection members 150, connection tabs 160, and a fixing member.

The first pulley 110 is disposed at one end of the robot arm 100, and the second pulley 120 is disposed at the other end of the robot arm 100. In addition, the first pulley 110 and the second pulley 120 may be connected via the strap unit 130. The first pulley 110 may be spaced apart a certain distance from the second pulley 120.

The first pulley 110 may have a cylindrical shape having a curved portion in the outer side thereof so that the strap unit 130 may be wound on the outer side thereof. The first pulley 110 may have a certain diameter.

The first pulley 110 may be supplied with the driving force and is rotated, and may be rotated about a first central hole 110H thereof as a center axis. The first pulley 110 may have a protrusion 111 on the center thereof, and the protrusion 111 may have the first central hole 110H penetrating therethrough. The robot arm 100 may transfer the driving force to a neighboring robot arm or may be supplied with the driving force from a neighboring robot arm via the first central hole 110H provided in the first pulley 110.

The first pulley 110 may have a seating groove on which the block unit 140 is attached, in one side thereof. A shape or volume of the seating groove may be set according to a size or a shape of the block unit 140 attached thereto. For example, a first block 141 and a fourth block 144 may be attached to the seating groove of the first pulley 110.

Referring to FIG. 6, the first pulley 110 has a cross-section that is bent in an L-shape at one side thereof, and respective surfaces of the bent cross-section may be defined as a first seating surface 110A and a second seating surface 110B. One sides of the first block 141 and the fourth block 144 may be respectively arranged to be adjacent to or come into contact with the first seating surface 110A. The second seating surface 110B has a surface corresponding to the shape of the block unit 140 seated thereon, and may have a greater area than a contact area of the block unit 140 seated thereon so as not to interfere with the movement of the first block 141, of which the position is adjusted.

The second pulley 120 is spaced apart from the first pulley 110 and may be disposed on the other side of the robot arm 100. The second pulley 120 may be formed to be substantially the same as the first pulley 110.

For example, the second pulley 120 may have a certain diameter. The second pulley 120 has a protrusion at the center thereof, and the protrusion may have a second central hole 120H penetrating therethrough.

The second pulley 120 may have a seating groove to which a second block 142 and a third block 143 are attached. The second pulley 120 may have a seating groove in one side thereof, to which the block unit 140 is attached, and the second block 142 and the third block 143 may be attached to the seating groove of the second pulley 120.

The strap unit 130 may connect the first pulley 110 to the second pulley 120. The strap unit 130 may be at least partially wound on the first pulley 110 and the second pulley 120. The strap unit 130 may be attached so that some parts of the outer circumferences of the first pulley 110 and the second pulley 120 are covered. The strap unit 130 connects the driving shaft of the rotating first pulley 110 to the driving shaft of the second pulley 120 so as to transfer a torque from an active shaft to a driven shaft.

In an embodiment, the strap unit 130 is provided as a pair including a first strap 131 and a second strap 132.

One end of the first strap 131 may be connected to the first pulley 110 and the other end of the first strap 131 may be connected to the second pulley 120. One end of the first strap 131 is attached to the first block 141 and the other end of the first strap 131 is attached to the second block 142.

In an embodiment, a position of one end of the first strap 131 is adjustable by the first block 141, and the other end of the first strap 131 may be fixed to the second pulley 120 by the second block 142. Although not shown in the drawings, the arrangement of the first block 141 and the second block 142 may be deformable. For example, the position of one end of the first strap 131 is fixed to the first pulley 110 by the first block 141, and the position of the other end of the first strap 131 may be adjustable on the second pulley 120 by the second block 142. A position of the second block 142 to which the other end of the first strap 131 is attached may be adjustable on the second pulley 120.

One end of the second strap 132 may be connected to the second pulley 120 and the other end of the second strap 132 may be connected to the first pulley 110. One end of the second strap 132 is attached to the third block 143 and the other end of the second strap 132 is attached to the fourth block 144.

A position of one end of the second strap 132 may be adjustable on the second pulley 120 by the third block 132, and the other end of the second strap 132 may be fixed to the first pulley 110 by the fourth block 144.

Although not shown in the drawings, the arrangement of the third block 143 and the fourth block 144 may be deformable. For example, one end of the second strap 132 may be connected to the second pulley 120 by the third block 143 and the position of the other end of the second strap 132 may be adjustable on the first pulley 110 by the fourth block 144. A position of the fourth block 144 to which the other end of the second strap 132 is attached may be adjustable on the first pulley 110.

Hereinafter, for convenience of description, an embodiment in which the positions of the first block 141 and the third block 143 may be adjusted by the pulleys and the positions of the second block 142 and the fourth block 144 are fixed to the pulley will be described below.

The strap unit 130 may be formed of a metal material including stainless steel, tungsten, an ultra-elastic alloy, etc., and may have various materials according to the usage thereof.

The block unit 140 may connect the strap unit 130 to the first pulley 110 or to the second pulley 120. The block unit 140 may be disposed on both ends of the first strap 131 or the second strap 132.

In an embodiment, the block unit 140 may include the first block 141, the second block 142, the third block 143, and the fourth block 144.

A position of one of the block unit 140 disposed at the both ends of the first strap 131 may be fixed, but a position of the other may be adjustable. When the position of the block unit 140 is adjusted, a tension of the first strap 131 may be adjusted.

The first block 141 is attached to the first pulley 110 and may be connected to one end of the first strap 131. The position of the first block 141 may be adjusted on the first pulley 110. The second block 142 is attached to the second pulley 120, and may be connected to the other end of the first strap 131 and the position thereof may be fixed on the second pulley 120.

The third block 143 is attached to the second pulley 120 and may be connected to one end of the second strap 132. The position of the third block 143 may be adjustable on the second pulley 120. The fourth block 144 is attached to the first pulley 110, and may be connected to the other end of the second strap 132 and the position thereof may be fixed on the first pulley 110. For example, the first block 141 is arranged on the first pulley 110 as a pair along with the fourth block 144, and the second block 142 may be arranged on the second pulley 120 as a pair along with the third block 143. Hereinafter, the first block 141 and the fourth block 144 will be described for convenience of the description.

The first block 141 and the fourth block 144 have symmetrical shapes and may be seated on the first pulley 110.

The first block 141 may include a 1A surface 141A, a 1B surface 141B, a 1C surface 141C, a 1D surface 141D, and a 1E surface 141E.

The 1A surface 141A may face a 4A surface 144A of the fourth block 144. The 1B surface 141B may provide a region to which one end of the first strap 131 is attached. The 1C surface 141C may form a curve so as to come into contact with and to be wound by the first strap 131. Because the 1C surface 141C has a curve, the first strap 131 may be attached to the first block 141 with a curvature that is similar to, substantially the same as, that of the first pulley 110. The 1D surface 141D and the 1E surface 141E are cut at the edges of the first block 141 and may prevent the damage to the first strap 131 when adjusting the position of the first block 141.

The fourth block 144 may have the 4A surface 144A, a 4B surface 144B, a 4C surface 144C, and a 4D surface 144D. The 4A surface 144A, the 4B surface 144B, the 4C surface 144C, and the 4D surface 144D are substantially the same as the 1A surface 141A, the 1B surface 141B, the 1C surface 141C, and the 1D surface 141D of the first block 141.

However, the shape of the block unit 140 shown in the drawings is an example, and one or more embodiments are not limited thereto. The shape of the block unit 140 may be variously set according to shapes of the first pulley 110 and the second pulley 120.

The position of one of the block unit 140 disposed at the both ends of the second strap 132 may be fixed, but the position of the other may be adjustable. When the position of the block unit 140 is adjusted, a tension of the second strap 132 may be adjusted.

The block unit 140 may be disposed in each of the seating groove of the first pulley 110 and the seating groove of the second pulley 120. Referring to FIG. 4, the seating groove of the first pulley 110 and the seating groove of the second pulley 120 may be arranged in opposite directions to each other.

For example, the seating groove of the first pulley 110 may be disposed at a left end portion of the first pulley 110 and the seating groove of the second pulley 120 may be disposed at a right end portion of the second pulley 120. Due to the above arrangement, the first block 141 and the fourth block 144 are arranged at the left side of the first pulley 110, and the second block 142 and the third block 143 are arranged at the right side of the second pulley 120. The block units 140 are respectively arranged on the first pulley 110 and the second pulley 120 to be symmetrical with each other, so as to prevent the robot arm 100 from being twisted or the driving force from being biased to a certain direction during transferring the driving force.

An outer circumference of the block unit 140 may have a certain curvature so as to extend on the outer circumferences of the first pulley 110 and the second pulley 120. The outer circumference of the block unit 140 may have a curved surface on which the strap unit 130 is wound. For example, the 1C surface 141C of the first block 141 and the 4C surface 144C of the fourth block 144 are formed to correspond to the curvature of the first pulley 110, and thus, the first strap 131 and the second strap 132 may be attached to the first block 141 and the fourth block 144 with a certain curvature, that is, the curvature of the first pulley 110.

The first pulley 110 and the first block 141 or the first pulley 110 and the fourth block 144 may be connected to each other via a first fixing member 171 and a second fixing member 172.

The first block 141 is seated on the first pulley 110 and forms a height that is substantially the same as that of the upper surface of the first pulley 110, and may have a groove spaced a certain distance from the upper surface. In the groove, a first elongated hole 141H that is through and through to the lower surface may be provided. The first block 141 may be moved as much as a set size of the first elongated hole 141H by using the first fixing member 171 as a movement axis.

The first block 141 and the fourth block 144 may be integrally connected to each other via the connection member 150. For example, the first block 141 may include a first block protrusion 1410 and a first through hole 1410H. The first block protrusion 1410 protrudes from the upper surface of the first block 141 and may be provided to have the first through hole 1410H having depth in which the connection member 150 may be inserted. The fourth block 144 facing the first block 141 may include a second block protrusion 1440 and a second through hole 1440H. The connection member 150 may be inserted into each through-hole from the fourth block 144 toward the first block 141. The connection member 150 installed on the second pulley 120 may be inserted into the through holes from the second block 142 toward the third block 143.

In an embodiment, the connection member 150 may be arranged so as to adjust the moving distance of the first block 141 or the third block 143. The connection member 150 may be fastened with the block unit 140 via a fastening unit such as a bolt.

The connection member 150 may be supported by the first pulley 110 and is partially inserted in the first block 141 so as to adjust the position of the first block 141. For example, the connection member 150 may be coupled through a screw coupling hole formed in a part of the block unit 140.

In detail, the connection member 150 may be provided between the first block 141 and the fourth block 144 arranged on the first pulley 110, and may be provided between the second block 142 and the third block 143 arranged on the second pulley 120. For example, a distance between the first block 141 and the fourth block 144 may be increased or decreased as much as a moving distance of the connection member 150. The distance between the second block 142 and the third block 143 may be adjusted in the same manner, but the progress directions of the connection members 150 applied to the first block 141 and the second block 142 may be opposite to each other.

The strap unit 130 and the block unit 140 may be fixed by the connection tabs 160. The connection tab 160 includes a tab hole 161 formed through the center thereof, and a fastening unit such as a bolt, a nut, etc. for connecting to the strap unit 130 and the 1B surface 141B may be provided inside the tab hole 161.

The connection tab 160 may be arranged between one end of the first strap 131 and the first block 141 to fix the first strap 131. A first strap hole 131H of the first strap 131 may be aligned perpendicular to the lower end of the tab hole 161 and the first strap 131 may be fixed to the first block 141.

The connection tab 160 may be arranged between the other end of the second strap 132 and the fourth block 144 to fix the second strap 132. A second strap hole 132H of the second strap 132 may be aligned at the lower end of the tab hole 161 like the first strap hole 131H. Here, a lower surface of the connection tab 160 comes into contact with the upper surface of the strap unit 130 and may be fixed via a fastening unit such as a bolt, etc. inserted in the through hole.

In detail, a first support side 160a of the connection tab 160 is supported by a first stopper protrusion 141a of the first block 141, and a second support side 160b of the connection tab 160 may be supported by a second stopper protrusion 141b of the second block 142. As described above, the strap may be stably fixed due to the engagement structure between the connection tab 160 and the first and fourth blocks 141 and 144.

The fixing member may be disposed on each block so as to fix the block unit 140 to the first pulley 110 and the second pulley 120. The fixing member may include a first fixing member 171 and a second fixing member 172.

The first fixing member 171 is inserted into the first block 141 or the third block 143, and the second fixing member 172 may be inserted into the second block 142 or the fourth block 144. Hereinafter, for convenience of description, an embodiment in which the first fixing member 171 is inserted in the first block 141 and the second fixing member 172 is inserted in the fourth block 144 will be described below.

The first fixing member 171 is inserted into the first elongated hole 141H and the second fixing member 172 may be inserted in the hole 144H. End portions of the first fixing member 171 and the second fixing member 172 may be disposed through the first block 141 and the fourth block 144 so as to reach the second seating surface 110B.

For example, the first fixing member 171 guides the movement direction of the first block 141 and controls the first block 141 so as not to escape from the first pulley 110. Because the second fixing member 172 is inserted in the fourth block 144 and fixes the position of the fourth block 144, a reference for the movement passage of the first block 141 may be formed.

The arm assembly 11 for the surgical robot according to the present disclosure includes a driving assembly provided with a driving pulley that is rotatable about a driving pulley axis. A driven assembly disposed on the same straight line has a driven pulley that is rotatable about an axis that is parallel to the driving pulley axis, and the strap unit 130 may be configured to be in cooperation with the corresponding driven pulley and driving pulley so as to rotate the driven pulley in response to the rotation of the driving pulley. The relationship between the driving pulley and the driven pulley may be set differently according to the connecting relationship of the arm assembly 11 for the surgical robot.

Figure 9:
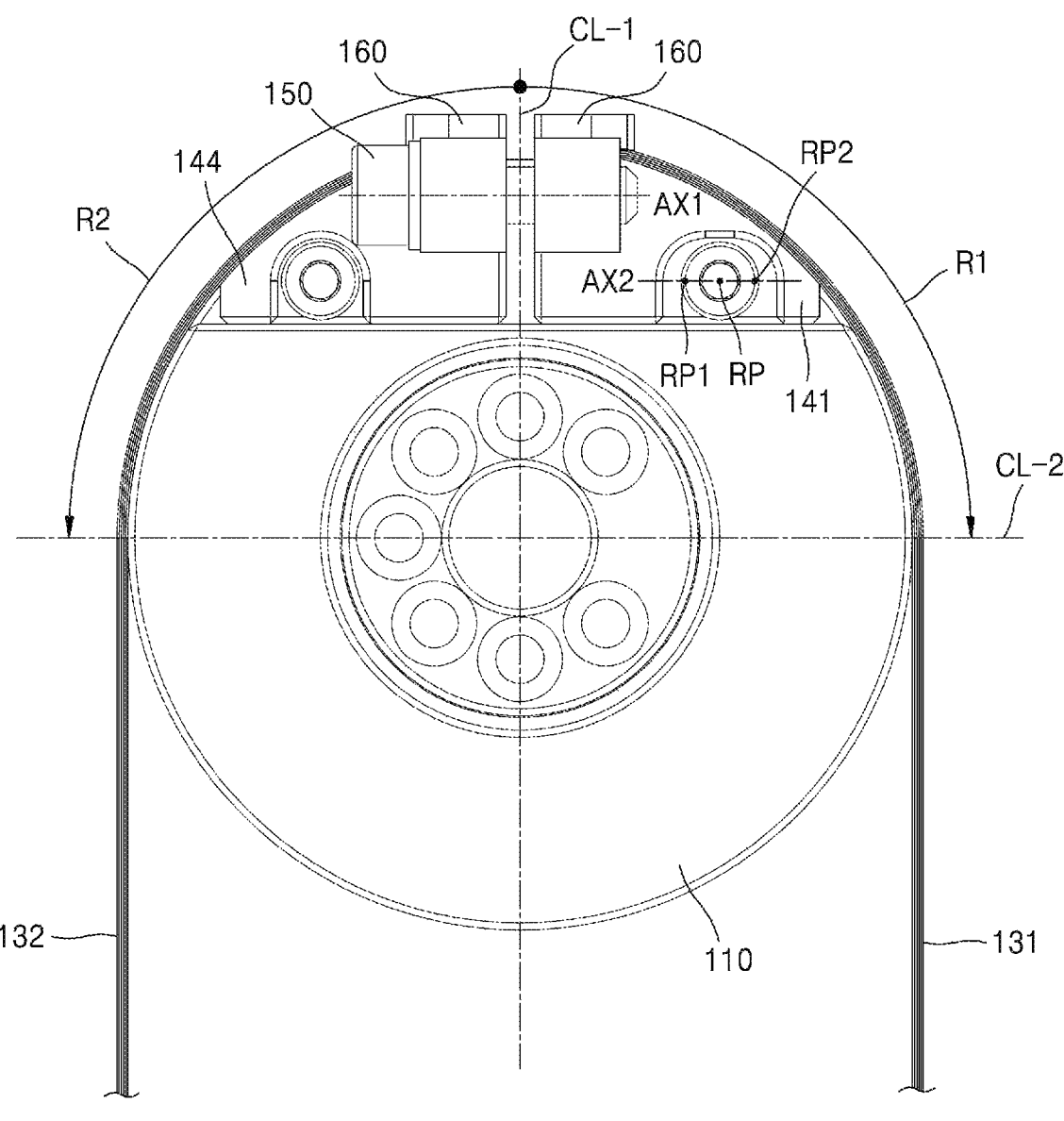
FIG. 9 is a diagram showing a moving passage of the arm assembly for the surgical robot of FIG. 4, in a process of adjusting a tension of a robot arm.
Figure 10:
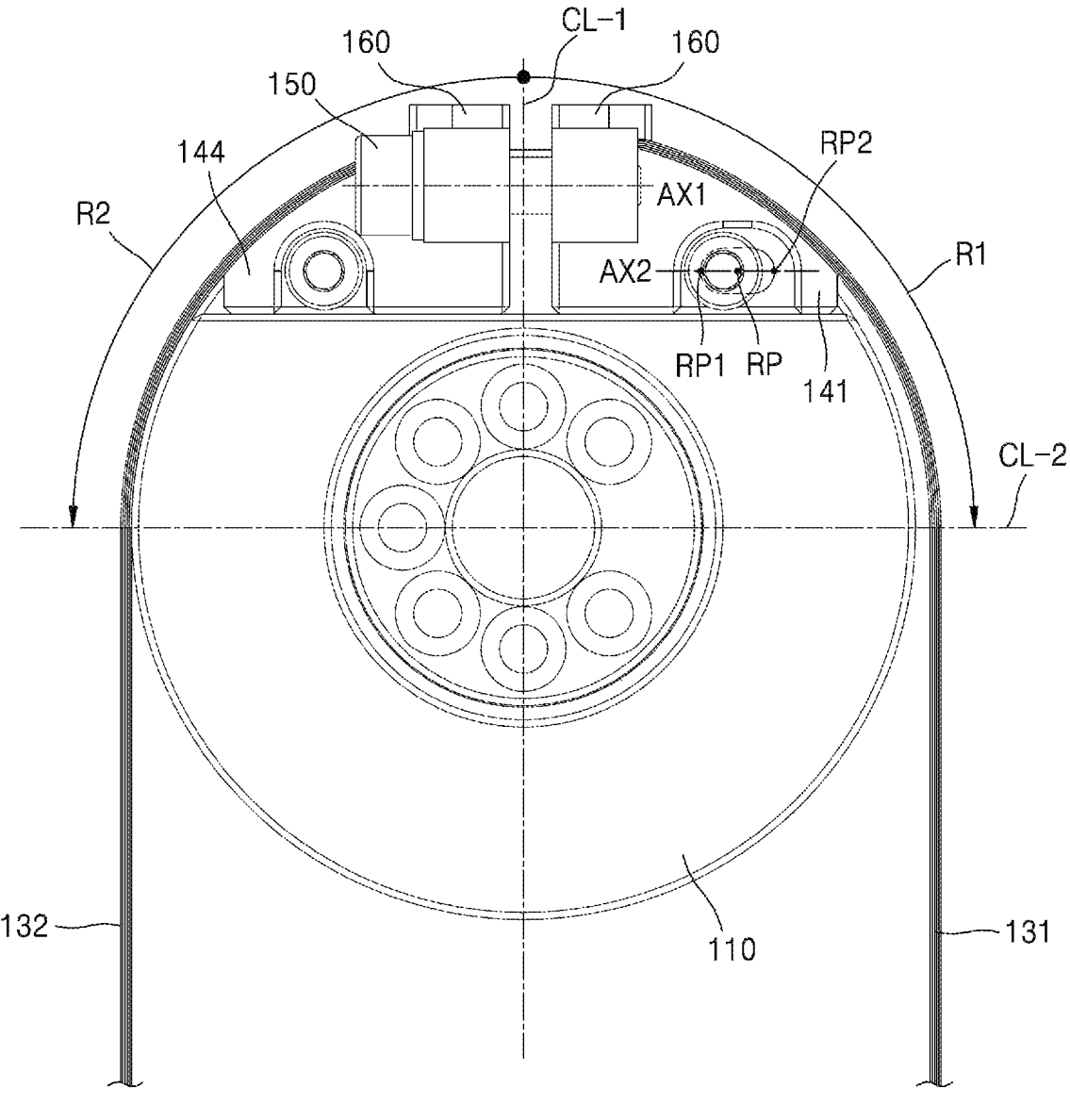
FIG. 10 is a diagram showing that the arm assembly for the surgical robot of FIG. 4 is moved to a first position.
Figure 11:
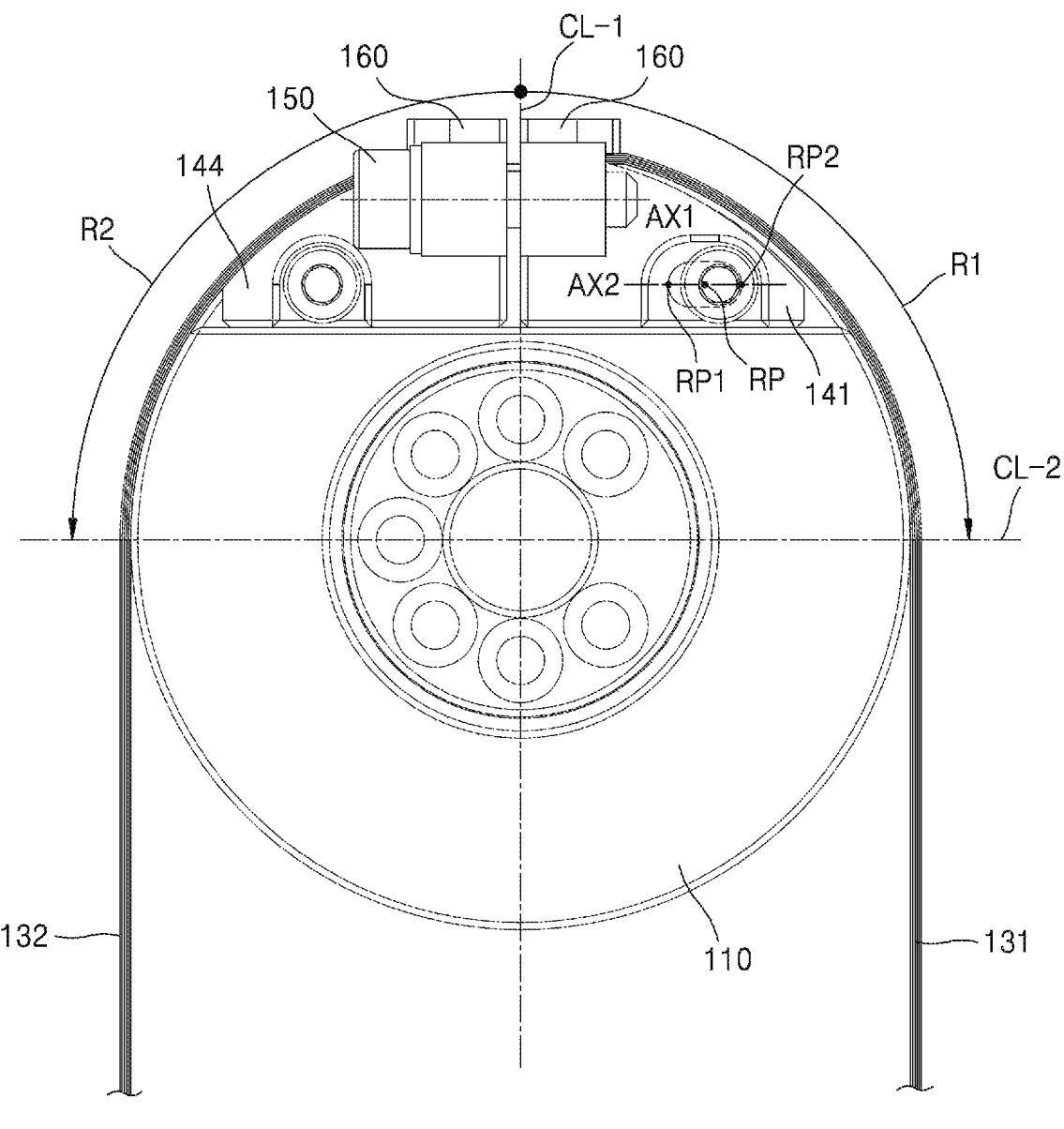
FIG. 11 is a diagram showing that the arm assembly for the surgical robot of FIG. 4 is moved to a second position.

FIG. 9 is a diagram showing a movement passage of the arm assembly for the surgical robot of FIG. 4 in a process of adjusting a tension of the robot arm, FIG. 10 is a diagram showing the arm assembly for the surgical robot of FIG. 4 moved to a first position, and FIG. 11 is a diagram showing the arm assembly for the surgical robot of FIG. 4 moved to a second position.

Referring to FIGS. 9 to 11, the first pulley 110 may be rotated in a clockwise direction or counter-clockwise direction based on a first center line CL-1. For example, the first pulley 110 and the second pulley 120 may be rotated in the clockwise direction or counter-clockwise direction in response to the movement of each robot arm or joint in the surgical robot.

The robot arm 100 may adjust the distance between the block units 140 facing each other by moving one of the block units 140. The tension of the strap unit 130 may be adjusted by the adjusting the distance between the block units 140 of the robot arm 100.

In the block unit 140, the connection member 150 is moved along a first axis AX to adjust the distance between the first block 141 and the fourth block 144. According to the movement of the connection member 150, the position of the first elongated hole 141H of the first block 141 may be adjusted. That is, because the connection member 150 is moved along a second axis AX2 of the first elongated hole 141H, the position of the first fixing member 171 on the second axis AX2 may be adjusted.

For example, as shown in FIG. 10, when the first block 141 is away from the first center line CL-1, the position of the first fixing member 171 on the second axis AX2 may be at a first position RP1. Also, as shown in FIG. 11, when the first block 141 is moved close to the first center line CL-1, the position of the first fixing member 171 may be at a second position RP2.

The first axis AX1 and the second axis AX2 may be in parallel to each other. Here, the second fixing member 172 may be fixed to the fourth block 144, and thus, when the connection member 150 is moved, the fourth block 144 may be firmly supported by the first pulley 110 due to the second fixing member 172.

As a surgical robot system performs a plurality of surgical operations, the strap unit 130 may be stretched or transformed to be loosened, and thus, a loss in the driving force transferred to the strap unit 130 may increase. Also, the change in the tension of the strap unit 130 may lead to the abrasion of the strap or operational errors of the instrument.

The robot arm 100 according to the present disclosure may easily and simply adjust and tune the tension of the strap unit 130. The robot arm 100 may adjust the tension of the strap by moving the strap unit 130 from a reference point.

For example, when the first block 141 is moved from a first reference point RP in the direction toward the first position RP1, the first strap 131 may be adjusted to increase the tension thereof. Also, when the first block 141 is moved from the first reference point RP in the direction toward the second position RP2, the first strap 131 is loosened and the tension decreases.

In the robot arm 100 according to the present disclosure, the end portion of the strap is disposed on the outside of the pulley, and thus, may not be excessively bent. Because the end portion of the strap extends along the outer surface of the pulley, even when the pulley is rotated repeatedly, a stress may not be concentrated onto a certain portion and the durability may be maintained.

In detail, the strap unit 130 is disposed to come into contact with the outermost portion of the first pulley 110. Because the strap unit 130 is naturally formed along the outer curves of the block unit 140 and the pulley, excessive stress may not be concentrated on a certain portion of the strap unit 130. That is, because the strap unit 130 is formed along the periphery of the first pulley 110, the driving force may be transferred without generating folding of the strap unit 130 according to the rotation of the first pulley 110.

Accordingly, the arm assembly 11 for the surgical robot may apply the rotating force that is required by the joint of each link connected to the manipulator 10, and the excessive folding amount of the strap unit 130 may be prevented with a simple structure, and thus, abrasion and aging of the strap unit 130 may be prevented.

The arm assembly 11 for the surgical robot may redistribute the tension transferred to each robot arm of the surgical robot and changes the movement axis, and thus, an appropriate tension may be generated according to the usage thereof.

The arm assembly 11 for the surgical robot according to the present disclosure may miniaturize the connecting structure between the strap unit 130 and each pulley, and thus may contribute to the miniaturization of the surgical robot system with a simple structure. Also, the abrasion of the strap unit 130 may be prevented, and thus, reliability of the surgical robot may be improved.

While the disclosure has been described with reference to exemplary embodiments thereof, it will be understood by those of ordinary skill in the art that various changes in form and details may be made therein without departing from the spirit and scope of the disclosure. Although not described, it would be appreciated that equivalent units may be coupled to the disclosure. Therefore, the scope sought to be protected of the disclosure shall be defined by the appended claims.

The arm assembly for the surgical robot according to the present disclosure may easily and simply adjust and tune the tension of the strap unit. The robot arm may adjust the tension of the strap by moving the strap unit from the reference point, and may stably transfer the driving force required by the instrument through the strap.

According to the arm assembly for the surgical robot of the present disclosure, because the end portion of the strap extends along the curvature of the pulley, even when the pulley is rotated repeatedly, the stress may not be concentrated onto a certain portion of the strap and the durability of the strap may be maintained.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. An arm assembly for a surgical robot having a plurality of robot arms, the arm assembly comprising:

a first pulley attached to one side of the robot arm and to which first block and a fourth block are attached;

a second pulley attached to the other side of the robot arm to be spaced apart from the first pulley;

a first strap of which one end is connected to the first block and the other end is connected to the second pulley;

a second strap of which one end is connected to the fourth block and the other end is connected to the second pulley;

a connection member that is supported by the first pulley and is partially inserted in the first block and the fourth block so as to adjust a distance between the first block and the fourth block; and a pair of connection tabs that are respectively attached to one end of the first strap and one end of the second strap so as to fix the first strap to the first block and to fix the second strap to the fourth block, wherein a supporting side of each of the pair of connection tabs is supported by stopper protrusions of the first block and the fourth block so as to form an engagement structure with the first block and the fourth block, thereby supporting a distance between the one ends of the first strap and the second strap.

2. The arm assembly of claim 1, wherein one end of the first strap extends along a surface of the first block, and the other end of the first strap extends along a surface of the second block.

* * * * *